US00PP32882P2

(12) United States Plant Patent
Arts

(10) Patent No.: US PP32,882 P2
(45) Date of Patent: Mar. 9, 2021

(54) ***HYDRANGEA* PLANT NAMED 'HP219902'**

(50) Latin Name: *Hydrangea paniculata*
Varietal Denomination: HP219902

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 16/873,546

(22) Filed: Apr. 30, 2020

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Hydrangea* plant named 'HP219902', characterized by its upright to somewhat outwardly spreading and rounded to conical plant habit; vigorous growth habit and moderate growth rate; freely branching habit with strong, thick and sturdy stems that are reddish brown in color; freely and uniformly flowering habit; large inflorescences with numerous yellow green-colored sterile flowers that maintain their yellow green-color in the autumn; and good garden performance.

2 Drawing Sheets

Figure 1:
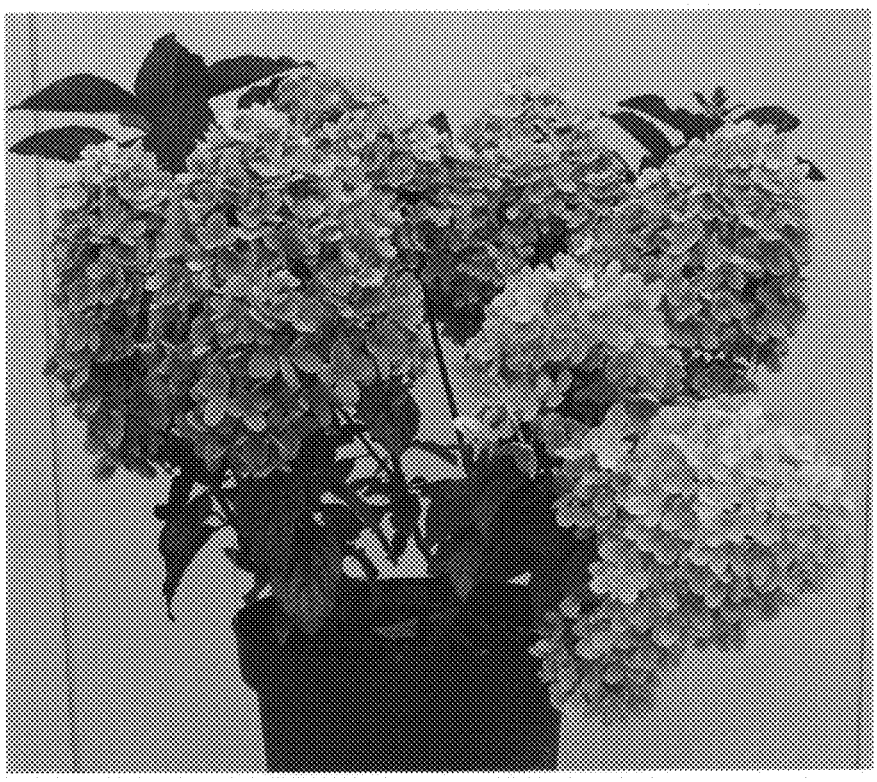

Botanical designation: *Hydrangea paniculata.*
Cultivar denomination: 'HP219902'.

CROSS-REFERENCED TO CLOSELY-RELATED APPLICATIONS

Title: *Hydrangea* Plant Named 'HP219901'
Inventor: Niels Arts
Filed: Concurrently with this application Ser. No. 16/873,544

STATEMENT REGARDING PRIOR DISCLOSURES BY INVENTOR & APPLICANT

An European Community Plant Breeder's Rights application for the instant plant was filed by the Applicant, *Hydrangea* Breeders Association B.V. of De Kwakel, The Netherlands, on Dec. 5, 2019, application number 2019/3317. Foreign priority is not claimed to this application.

The Inventor and Applicant assert that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea paniculata*, commercially referred to as a panicle *Hydrangea* and hereinafter referred to by the name 'HP219902'.

The new *Hydrangea* plant is a product of a planned breeding program conducted by the Inventor in De Kwakel, The Netherlands and Lengerich, Germany. The objective of the breeding program was to create new compact and freely-branching *Hydrangea* plants with strong sturdy stems, large inflorescences with numerous showy sterile flowers, attractive sterile flower color and good garden performance.

The new *Hydrangea* plant originated from a cross-pollination made by the Inventor in August, 2012 in De Kwakel, The Netherlands, of a proprietary selection of *Hydrangea paniculata* identified as code number 11-0007, not patented, as the female, or seed, parent with a proprietary selection of *Hydrangea paniculata* identified as code number 11-0005, not patented, as the male, or pollen, patent. The new *Hydrangea* plant was discovered and selected by the Inventor as a single flowering plant from within the progeny of the stated cross-pollination in a controlled greenhouse environment in Lengerich, Germany in September, 2014.

Asexual reproduction of the new *Hydrangea* plant by vegetative tip cuttings in a controlled environment in De Kwakel, The Netherlands since March, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HP219902'. These characteristics in combination distinguish 'HP219902' as a new and distinct *Hydrangea* plant:

1. Upright to somewhat outwardly spreading and rounded to conical plant habit.
2. Vigorous growth habit and moderate growth rate.
3. Freely branching habit with strong, thick and sturdy stems that are reddish brown in color.
4. Freely and uniformly flowering habit.
5. Large inflorescences with numerous yellow green-colored sterile flowers that maintain their yellow green-color in the autumn.
6. Good garden performance.

Plants of the new *Hydrangea* can be compared to plants of the female parent selection. Plants of the new *Hydrangea* differ primarily from plants of the female parent selection in flowering response as plants of the new *Hydrangea* flower later than plants of the female parent selection.

Plants of the new *Hydrangea* can be compared to plants of the male parent selection. Plants of the new *Hydrangea* differ primarily from plants of the male parent selection in inflorescence size as plants of the new *Hydrangea* have larger inflorescences than plants of the male parent selection.

Plants of the new *Hydrangea* can be compared to plants of the *Hydrangea paniculata* 'HP219901', disclosed in a U.S. Plant Patent application filed concurrently. In side-by-side comparisons, plants of the new *Hydrangea* differ primarily from plants of 'HP219901' in the following characteristics:

1. Plants of the new *Hydrangea* are smaller than plants of 'HP219901'.
2. Plants of the new *Hydrangea* are not as freely branching as plants of 'HP219901'.
3. Plants of the new *Hydrangea* have slightly smaller leaves than plants of 'HP219901'.
4. Plants of the new *Hydrangea* have slightly smaller inflorescences with fewer fertile and sterile flowers than plants of 'HP219901'.
5. Sterile flowers of inflorescences of plants of the new *Hydrangea* maintain their yellow green color in the autumn whereas sterile flowers of inflorescences of plants of 'HP219901' become blushed with dark pink in the autumn.

Plants of the new *Hydrangea* can also be compared to plants of the *Hydrangea paniculata* 'HP217902', disclosed in U.S. Plant Pat. No. 30,332. In side-by-side comparisons, plants of the new *Hydrangea* differ primarily from plants of 'HP217902' in the following characteristics:

1. Plants of the new *Hydrangea* are more vigorous than and not as compact as plants of 'HP217902'.
2. Lateral branches of plants of the new *Hydrangea* are sturdier and stronger than lateral branches of plants of 'HP217902'.
3. Plants of the new *Hydrangea* flower about three weeks later than plants of 'HP217902'.
4. Inflorescences of plants of the new *Hydrangea* are larger with many more sterile and fertile flowers than inflorescences of plants of 'HP217902'.
5. Sterile flowers of inflorescences of plants of the new *Hydrangea* maintain their yellow green color in the autumn whereas sterile flowers of inflorescences of plants of 'HP217902' become purplish pink in the autumn.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'HP219902' grown in a container.

Figure 2:
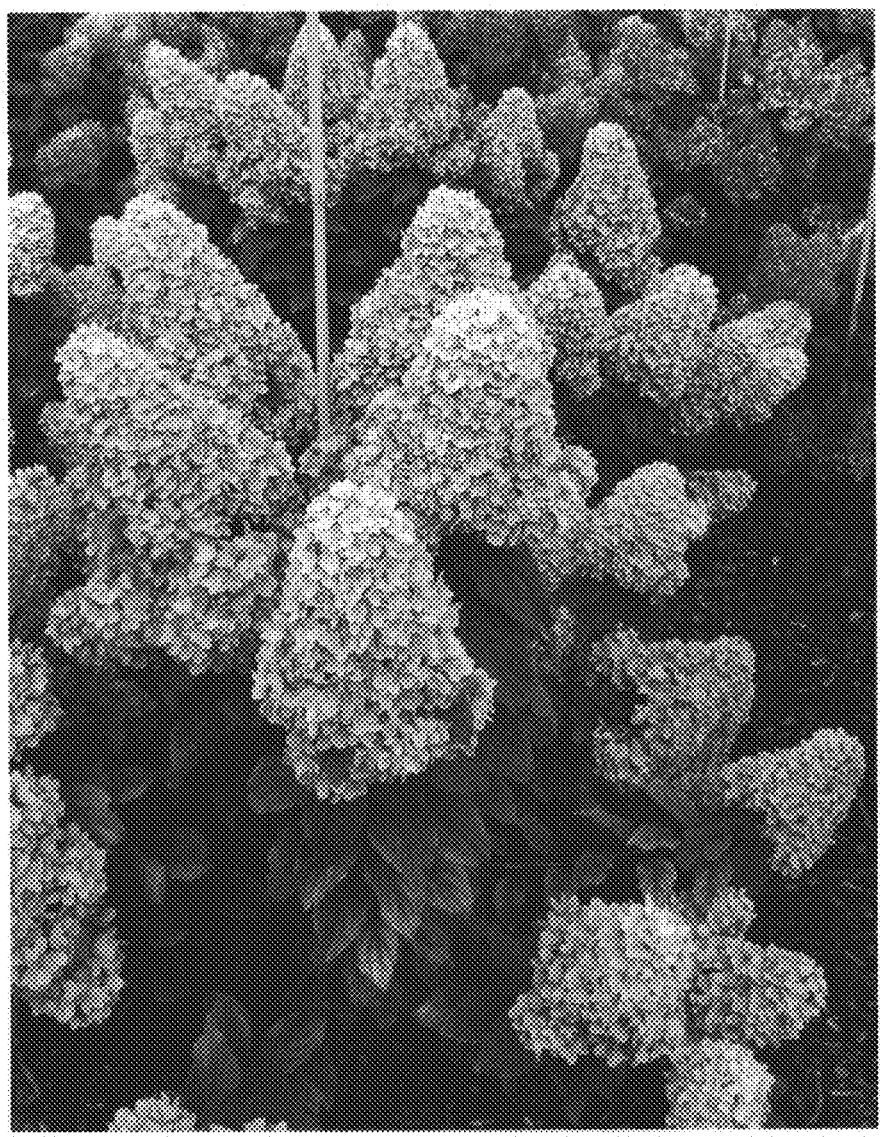

The photograph on the second sheet (FIG. 2 of 2) is a side perspective view of a typical flowering plant of 'HP219902' grown during the autumn.

DETAILED BOTANICAL DESCRIPTION

Plants used in the aforementioned photographs and in the following description were grown during the late summer and autumn in 27-cm containers in an outdoor nursery in Lengerich, Germany and under cultural practices typical of commercial panicle *Hydrangea* production. During the production of the plants, day and night temperatures averaged 15° C. Plants of the new *Hydrangea* 18 months old when the photograph (FIG. 1 of 2) and description were taken and 21 months old when the photograph (FIG. 2 of 2) and autumnal color values were taken. In the following description, color references are made to The Royal Horticultural Society Colour Chart, 2015 Edition, except where general terms of ordinary dictionary significance are used.

Botanical description: *Hydrangea paniculata* 'HP219902'.

Parentage:

*Female, or seed, parent.*—Proprietary selection of *Hydrangea paniculata* identified as code number 11-0007, not patented.

*Male, or pollen, parent.*—Proprietary selection of *Hydrangea paniculata* identified as code number 11-0005, not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 18° C.

*Time to produce a rooted young plant, summer.*—About four weeks at temperatures about 23° C.

*Time to produce a rooted young plant, winter.*—About five weeks at temperatures about 18° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright to somewhat outwardly spreading and rounded to conical plant habit; strong and sturdy stems; vigorous growth habit and moderate growth rate.

*Plant height.*—About 48 cm to 55 cm.

*Plant diameter or area of spread.*—About 57 cm to 62 cm.

Lateral branch description:

*Branching habit.*—Freely branching habit; when pinched, about 10 to 14 lateral branches develop per plant.

*Length, stem axis to base of inflorescence.*—About 26 cm to 38 cm.

*Diameter*.—About 6 mm to 7 mm.
*Internode length*.—About 3.5 cm to 4.5 cm.
*Texture*.—Smooth, glabrous; fully developed, woody.
*Aspect*.—Mostly upright.
*Strength*.—Strong, sturdy.
*Color*.—When developing: Close to 145B to 145C; lenticels, close to 165C. Developed: Close to 176B; lenticels, close to 165C.

Leaf description:
*Arrangement*.—Opposite, simple.
*Length*.—About 7 cm to 10 cm.
*Width*.—About 4.5 cm to 6 cm.
*Shape*.—Ovate.
*Apex*.—Acute.
*Base*.—Obtuse.
*Margin*.—Serrulate.
*Texture, upper surface*.—Rugose; pubescent.
*Texture, lower surface*.—Prominent venation; glabrous.
*Venation pattern*.—Pinnate.
*Color*.—Developing leaves, upper surface: Close to between 137A and 138A. Developing leaves, lower surface: Close to 138B. Fully developed leaves, upper surface: Close to 137B; venation, close to 144B. Fully developed leaves, lower surface: Close to 138B; venation, close to 145C.
*Petioles*.—Length: About 1 cm to 1.5 cm. Diameter: About 2 mm to 2.5 mm. Texture, upper and lower surfaces: Smooth, glabrous. Color, upper surface: Close to 145B tinged with close to 178B. Color, lower surface: Close to 145C tinged with close to 178B.

Flower description:
*Flower type and habit*.—Showy sterile flowers and small fertile flowers arranged on terminal panicles; panicles broadly pyramidal in shape; flowers face upright to outwardly depending on their position in the inflorescence.
*Fragrance*.—Faint, pleasant.
*Natural flowering season*.—Plants begin flowering about 18 weeks after planting; flowering begins in the early summer and is continuous throughout the summer in Northern Europe.
*Flower longevity*.—Fertile flowers last about one month on the plant, fertile flowers not persistent; sterile flowers last about three months on the plant, sterile flowers persistent.
*Quantity of flowers*.—Freely flowering habit; about 500 to 600 fertile flowers develop per panicle and about 1,000 to 1,200 sterile flowers develop per panicle.
*Panicle height*.—About 23 cm to 25 cm.
*Panicle diameter*.—About 18 cm to 23 cm.
*Fertile flower buds*.—Length: About 3 mm. Diameter: About 2 mm. Shape: Rounded. Color: Close to 145C and 157A.
*Sterile flower buds*.—Length: About 3 mm. Diameter: About 2 mm. Shape: Rounded. Color: Close to 145A.
*Fertile flower diameter*.—About 3 mm.
*Fertile flower depth* (*height*).—About 3 mm.
*Sterile flower diameter*.—About 2 cm to 2.5 cm.
*Sterile flower depth* (*height*).—About 3 mm.
*Petals, fertile flowers*.—Quantity and arrangement: About four or five in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 157D. Fully opened, upper and lower surfaces: Close to 157D; color does not change with development.
*Petals, sterile flowers*.—Quantity and arrangement: About three or four in a single whorl. Length: About 1.5 mm. Width: About 1 mm. Shape: Ovate. Apex: Acute. Base: Cuneate. Margin: Entire. Texture, upper and lower surfaces: Smooth, glabrous. Color: When opening, upper and lower surfaces: Close to 157D. Fully opened, upper and lower surfaces: Close to 157D; color does not change with development.
*Sepals, fertile flowers*.—Quantity and arrangement: About four or five in a single whorl. Length: About 1 mm. Width: About 1 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145C; color does not change with development.
*Sepals, sterile flowers*.—Quantity and arrangement: About four in a single whorl; slightly imbricate. Length: About 1 cm to 1.5 cm. Width: About 0.75 cm to 1.25 cm. Shape: Elliptic to oval. Apex: Obtuse to slightly retuse. Base: Obtuse to cuneate. Margin: Entire. Texture, upper and lower surfaces: Smooth, glabrous. Color: When opening, upper and lower surfaces: Close to 145A. Fully opened, upper and lower surfaces: Close to between 145D and 150D; in the autumn, color becoming closer to 145C.
*Pedicels, fertile flowers*.—Length: About 3 mm. Diameter: About 1.5 mm. Strength: Strong. Aspect: Mostly upright. Texture: Smooth, glabrous. Color: Close to 145C.
*Pedicels, sterile flowers*.—Length: About 1. cm to 1.5 cm. Diameter: About 1.5 mm. Strength: Strong. Aspect: About 80° to 90° from branch axis. Texture: Smooth, glabrous. Color: Close to 157C.
*Reproductive organs, fertile flowers*.—Stamens: Quantity per flower: About nine to ten. Filament length: About 3 mm. Filament color: Close to 157D. Anther length: About 1 mm. Anther shape: Round. Anther color: Close to 157D. Pollen amount: Moderate. Pollen color: Close to 84D. Pistils: Pistil quantity per flower: One. Pistil length: About 0.5 mm to 1 mm. Stigma shape: Three-lobed. Stigma color: Close to 157C. Style length: About 0.5 mm. Style color: Close to 157C. Ovary color: Close to 157C.
*Reproductive organs, sterile flowers*.—Stamens: Quantity per flower: About three to five. Filament length: About 3 mm. Filament color: Close to 157D. Anther length: About 1 mm. Anther shape: Round. Anther color: Close to 157D. Pollen amount: Scarce. Pollen color: Close to 84D. Pistils: To date, pistil development on sterile flowers has not been observed on plants of the new *Hydrangea*.
*Seeds, only produced by fertile flowers*.—Quantity per fertile flower: About 20 to 30. Length: Less than 0.5 mm. Diameter: Less than 0.5 mm. Color: Close to 200C.

Pathogen & pest resistance: To date, plants of the new *Hydrangea* grown under commercial production conditions have not been observed to be resistant to pathogens and pests common to *Hydrangea* plants.

Garden performance: Plants of the new *Hydrangea* have been shown to have good garden performance and to be tolerant to temperatures ranging from about −38° C. to about 38° C.

It is claimed:

1. A new and distinct *Hydrangea* plant named 'HP219902' as illustrated and described.

* * * * *